United States Patent [19]

Kohayakawa et al.

[11] Patent Number: 4,634,241
[45] Date of Patent: Jan. 6, 1987

[54] STEREOSCOPIC MICROSCOPE

[75] Inventors: Yoshimi Kohayakawa, Yokohama; Takashi Masuda, Kawasaki, both of Japan

[73] Assignee: Canon Kabushiki Kaisha, Tokyo, Japan

[21] Appl. No.: 724,883

[22] Filed: Apr. 19, 1985

[30] Foreign Application Priority Data

Apr. 27, 1984 [JP] Japan .................................. 59-62402
Aug. 22, 1984 [JP] Japan ................................. 59-127151

[51] Int. Cl.⁴ ............................................. G02B 21/22
[52] U.S. Cl. ...................................... 350/516; 350/139
[58] Field of Search ......................... 350/139, 130-131, 350/515-517, 550-555, 571; 356/12-14

[56] References Cited

U.S. PATENT DOCUMENTS

| 1,000,609 | 8/1911 | König ................................... 356/12 |
| 4,009,526 | 3/1977 | Abe et al. ............................. 350/139 |

FOREIGN PATENT DOCUMENTS

| 3117858 | 1/1982 | Fed. Rep. of Germany ...... 350/515 |
| 3429240 | 2/1985 | Fed. Rep. of Germany ...... 350/515 |
| 1410934 | 8/1965 | France ................................. 350/550 |
| 165113 | 12/1981 | Japan ................................... 350/515 |
| 652519 | 3/1979 | U.S.S.R. .............................. 350/555 |

Primary Examiner—William H. Punter
Attorney, Agent, or Firm—Fitzpatrick, Cella, Harper & Scinto

[57] ABSTRACT

A stereoscopic microscope is provided with a single objective lens and a pair of eyepieces disposed rearwardly of the objective lens. A pair of interpupillary distance adjusting means and a pair of refraction type vergence adjusting means are disposed between the objective lens and the eyepieces.

7 Claims, 5 Drawing Figures

STEREOSCOPIC MICROSCOPE

BACKGROUND OF THE INVENTION

1. Filed of the Invention

This invention relates to a stereoscopic microscope applied, for example, to the observation optical system of an ophthalmic slit lamp, and in particular to a stereoscopic microscope with a Galilean magnification changer.

2. Description of the Prior Art

The Galilean microscope and the binocular microscope have heretofore been widely used for the optical system of the magnification changer of this type. In the binocular microscope, entirely discrete two left and right microscopic optical systems are disposed so as to intersect each other at a predetermined angle, e.g., 10°-12°, and therefore, the problem of the vergence of the eyes does not occur. In this optical system, however, the objective lens is divided into two, that is, a pair of objective lenses are present and therefore, when interchanging the objective lenses for the purpose of magnification change, the handling thereof is complicated and cumbersome. Also, no part of the light beam becomes a parallel light and therefore, it is difficult to divide the optical paths of the side view mirror, the camera, etc. from half-way of the barrel.

On the other hand, the Galilean microscope is provided with a single objective lens and a pair of eyepieces, and the light beams passing through the eyepieces into the two eyes of the observer are parallel to each other and therefore, the angle of vergence is zero, while when observing with the microscope removed, the angle of vergence has a predetermined value and differs between the time when observation is effected through the microscope and the time when observation is effected without the intermediary of the microscope. Thus, with the Galilean microscope it is difficult to view stereoscopically. In this optical system, however, the light beam from a point on the subject body can be made into a parallel light beam by the objective lens and therefore, the magnification change of the optical system including a zoom optical system becomes simple, and also various accessories can be mounted by inserting a beam splitter into the parallel light beam portion.

Now, as a Galilean stereoscopic microscope in which vergence is taken into consideration, there is known one in which wedge prisms are disposed outside the eyepieces as proposed in Japanese Utility Model Publication No. 19530/1983, but in this type of microscope, prisms are present between the eyepieces and the examiner's eyes and this leads to a disadvantage that the examiner's eye points, i.e., pupil positions, become too near to the prisms to see, and also offers a problem in that chromatic aberration and astigmatism occur.

SUMMARY OF THE INVENTION

It is an object of the present invention to provide a stereoscopic microscope which very much facilitates the observation of a subject body by a simple construction.

It is another object of the present invention to provide a stereoscopic microscope which can prevent the occurrence of chromatic aberration attributable to the presence of refraction type vergence adjusting means.

DESCRIPTION OF THE PREFERRED EMBODIMENTS

Figure 1:
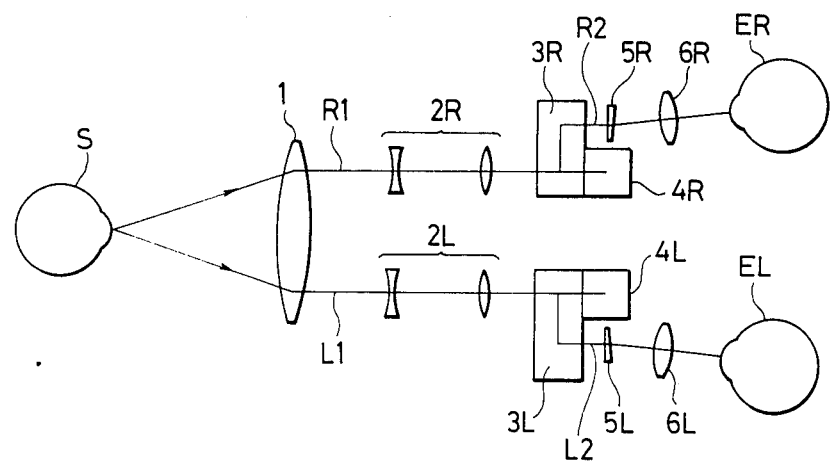
FIG. 1 shows a first embodiment of the present invention.

Referring to FIG. 1 which shows an embodiment in which the present invention is applied to an ophthalmic stereoscopic microscope, letter S designates an eye to be examined and letters EL and ER denote the observer's left eye and right eye, respectively. In the left and right optical paths of the microscope, there are disposed a common objective lens 1, imaging lenses 2L and 2R, image shaping prisms 3L and 3R, 4L and 4R, vergence adjusting wedge prisms 5L and 5R and eyepieces 6L and 6R.

The left and right optic axes L1 and R1 from the objective lens 1 to the image shaping prisms 3L and 3R are parallel to each other and magnification can be changed by moving the imaging lenses 2L and 2R. Also, light beams passing through the imaging lenses 2L and 2R are parallel light beams and therefore, it is also possible to suitably insert a light-dividing member and extract the light beams prior to photography by the use of the reflected oblique light at the light-dividing member.

Now, if the vergence adjusting wedge prisms 5L and 5R are disposed, it is possible to make the observation optic axes intersect each other at a predetermined angle by bending the optic axes L2 and R2 from the image shaping prisms 3L and 3R to the eyepieces 6L and 6R. Also, if the vergence adjusting wedge prisms 5L and 5R are disposed near the focal planes of the eyepieces 6L and 6R, chromatic aberration and astigmatism will not occur, and this is more convenient. If these vergence adjusting wedge prisms 5L and 5R are disposed at any other locations in the optical paths, the necessity of using a cemented achromatic prism will occur. In this regard, an embodiment in which vergence adjusting wedge prisms are disposed at parallel light beam portions will later be described by reference to FIG. 3.

Figure 2:
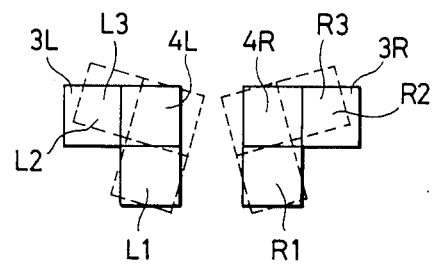
FIG. 2 is a view of image shaping prisms for vergence adjustment as seen from the direction of the optic axis.

FIG. 2 is a view of the image shaping prisms 3L and 3R of FIG. 1 as seen in the direction of the optic axes. Generally, an image shaping prism is constructed by combining two rectangular prisms and has the function of converting an inverted image into an erect image. In FIG. 2, dotted lines show a state in which the image shaping prisms 3L and 3R have been rotated about the optic axes L1 and R1 to adjust the interpupillary distance. In this state, the optic axis L2 becomes L3 and the optic axis R2 becomes R3 and therefore, the interpupillary distance can be adjusted from the interval between L2 and R2 to the interval between L3 and R3.

The vergence adjusting wedge prisms 5L and 5R are rotated with the image shaping prisms 3L and 3R during the adjustment of the interpupillary distance.

The vergence angle at a short sight is about 10° and therefore, assuming that the vergence angles are deflected by 5° each in FIG. 1 by the vergence adjusting wedge prisms 5L and 5R, if the direction of the line of sight when the image shaping prisms 3L and 3R have been rotated by 15° in FIG. 2 for the vergence adjustment is calculated, the vergence angle of horizontally 10° will change to 9.7° and the vergence angle of vertically 0° will change to an angle of depression of 1.3°, but such degree of change is practically negligible.

A second embodiment of the present invention will now be described.

Figure 3:
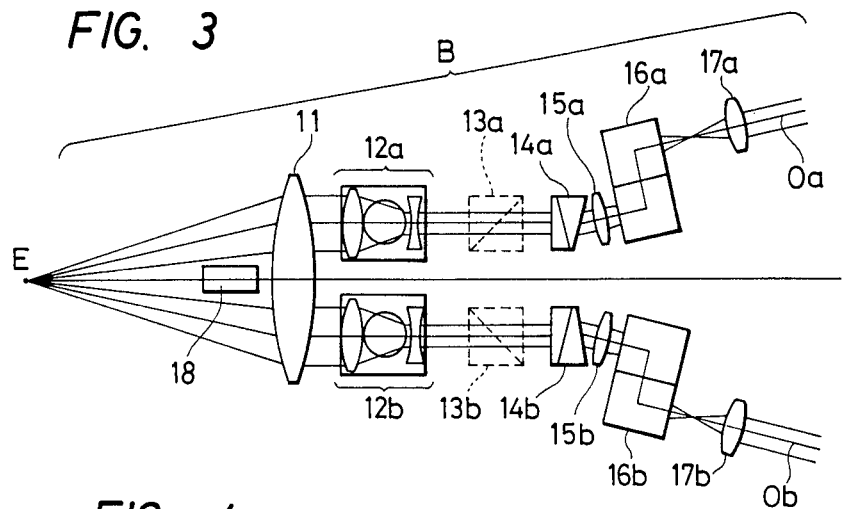
FIG. 3 shows a second embodiment of the present invention.

Referring to FIG. 3 which is a plan view showing only the magnification changer of a stereoscopic microscope, letters $O_a$ and $O_b$ designate optic axes corresponding to the observer's right eye and left eye, respectively. On these optic axes $O_a$ and $O_b$, there are successively disposed a common objective lens 11, magnification changing optical systems 12a, 12b, beam splitters 13a, 13b for dividing light to a photographing apparatus or a side view mirror, wedge type prisms 14a, 14b for deflecting the optical paths, relay lenses 15a, 15b, erect prisms 16a, 16b and eyepieces 17a, 17b. Forwardly of the objective lens 11, there is provided a light-dividing member 18 comprising a prism of an illuminating system which will later be described.

Figure 4:
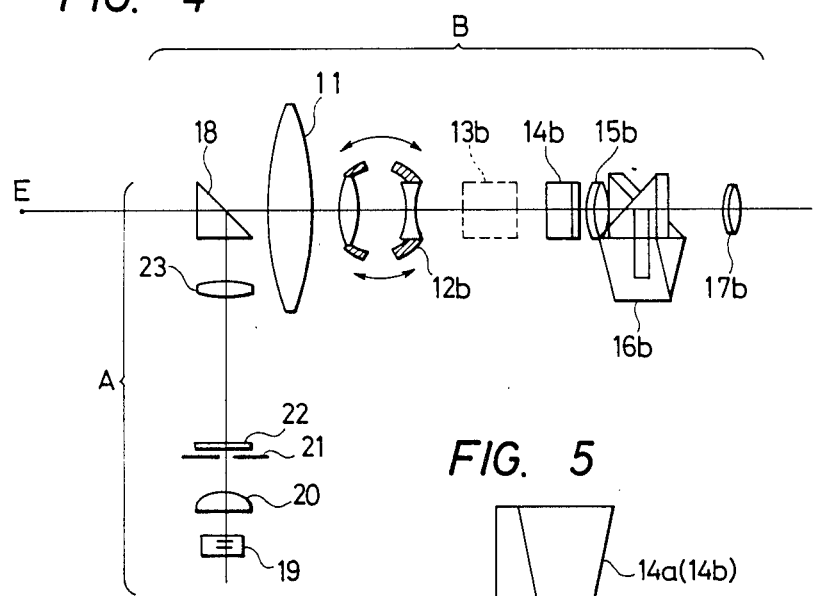
FIG. 4 shows the relation between a slit illuminating system and a magnification changer.
Figure 5:
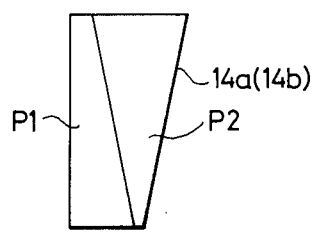
FIG. 5 is an enlarged view of a wedge type prism.

Referring to FIG. 4 which is a side view of the present embodiment, A designates a slit illuminating system and B denotes said magnification changer. The slit illuminating system A is comprised of an illuminating light source 19, a condenser lens 20, a slit 21, a filter 22, a projection lens 23 and the light-dividing member 18 disposed in succession. A light emitted from the illuminating light source 19 is condensed by the condenser lens 20, whereafter it illuminates the slit 21 and the image of this slit 21 is formed at the imaging position E of an eye to be examined by the projection lens 23 through the light-dividing member 18.

The slit 21, as is well known, has a mechanism which is capable of varying the width, height, etc. thereof. Also, the imaging position E of the slit 21 is made coincident with the object side focus position of the objective lens 11, and the light from the imaging position E is made into a parallel light beam by the objective lens 11 and this light beam has its magnification changed by the magnification changing optical systems 12a, 12b.

The magnification changing optical systems 12a, 12b together constitute a so-called Galilean telescope and the focus positions of the convex lenses and the concave lenses thereof are coincident with each other. If these magnification changing optical systems 12a, 12b are rotated as indicated by arrows in FIG. 4 and the convex lenses and the concave lenses thereof are replaced with each other, magnification will be varied. Light beams emerging from these magnification changing optical systems 12a, 12b are divided at a predetermined rate by the beam splitters 13a, 13b removably mountable in conformity with the intended purpose, whereafter they enter the wedge type prisms 14a, 14b.

Each of the wedge type prisms 14a and 14b is made, for example, by cementing two elements P1 and P2 together, one element P1 being made of crown glass of small dispersion and the other element P2 being made of flint glass of great dispersion so as to correct the difference in angle of refraction by wavelength. Accordingly, parallel light beams having emerged from the wedge type prisms 14a, 14b have their upper and lower parts and left and right parts mirror-inverted in the erect prisms 16a, 16b through the relay lens 15a, 15b and form slit images by the slit 20 at the focus positions of the eyepieces 17a, 17b. The observer can observe these slit images through the eyepieces 17a, 17b.

As described above, the stereoscopic microscope according to the present invention is meritorious in that the left and right optical paths are made into parallel light beams by the objective lens and magnification change and division of the optical paths can be accomplished simply. In addition the optic axes of the left and right eyepieces can be made to intersect each other at a predetermined angle by the refraction type vergence adjusting means to provide vergence by a simple construction and moreover no obstacle intervenes between the examiner and the eyepieces and the ease of observation can be maintained. the occurrence of chromatic aberration attributable to the presence of the refraction type vergence adjusting means can be prevented.

We claim:

1. A stereoscopic microscope comprising:
   a single objective lens;
   a pair of eyepieces disposed rearwardly of said objective lens;
   a pair of interpupillary distance adjusting means disposed between said objective lens and said eyepieces; and
   a pair of refraction type vergence adjusting means disposed between said objective lens and said eyepieces.

2. A stereoscopic microscope according to claim 1, wherein said vergence adjusting means are disposed near the focal planes of said eyepieces.

3. A stereoscopic microscope according to claim 2, wherein said vergence adjusting means are wedge type prisms.

4. A stereoscopic microscope according to claim 1, wherein said pair of refraction type vergence adjusting means are disposed in parallel light beam paths between said objective lens and said eyepieces.

5. A stereoscopic microscope according to claim 4, wherein said vergence adjusting means are wedge type prisms comprising two or more types of materials of different dispersions joined together.

6. A stereoscopic microscope having:
   a single objective lens;
   a pair of magnification changing optical systems disposed rearwardly of said objective lens;
   a pair of eyepieces disposed rearwardly of said magnification changing optical systems;
   a pair of interpupillary distance adjusting means disposed between said objective lens and said eyepieces; and
   a pair of refraction type vergence adjusting means disposed between said objective lens and said eyepieces.

7. A slit lamp comprising:
   illuminating means for illuminating a subject 15 with a slit-shaped light beam;
   an objective lens disposed in common to left and right eye observation optical paths;
   a pair of eyepieces disposed rearwardly of said objective lens;
   a pair of interpupillary distance adjusting means disposed between said objective lens and said eyepieces; and
   a pair of refraction type vergence adjusting means disposed between said objective lens and said eyepieces.

* * * * *